(12) United States Patent
Nauche et al.

(10) Patent No.: US 11,382,500 B2
(45) Date of Patent: Jul. 12, 2022

(54) OPTOMETRY DEVICE

(71) Applicant: ESSILOR INTERNATIONAL, Charenton-le-Pont (FR)

(72) Inventors: Michel Nauche, Charenton-le-Pont (FR); Stéphane Boutinon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 614 days.

(21) Appl. No.: 16/335,308

(22) PCT Filed: Sep. 20, 2017

(86) PCT No.: PCT/EP2017/073817
§ 371 (c)(1),
(2) Date: Mar. 21, 2019

(87) PCT Pub. No.: WO2018/054997
PCT Pub. Date: Mar. 29, 2018

(65) Prior Publication Data
US 2019/0274539 A1    Sep. 12, 2019

(30) Foreign Application Priority Data

Sep. 22, 2016 (EP) .................................. 16306224

(51) Int. Cl.
*A61B 3/032* (2006.01)
*A61B 3/00* (2006.01)

(52) U.S. Cl.
CPC ............ *A61B 3/032* (2013.01); *A61B 3/0008* (2013.01); *A61B 3/0041* (2013.01)

(58) Field of Classification Search
CPC ....... A61B 3/032; A61B 3/0008; A61B 3/145; A61B 3/12; A61B 3/14; A61B 3/103;
(Continued)

(56) References Cited

U.S. PATENT DOCUMENTS 4,298,253 A    11/1981  Tagnon
4,299,455 A *  11/1981  Aoki ...................... A61B 3/032
                                                            351/236

(Continued)

FOREIGN PATENT DOCUMENTS

CN    1255319 A    6/2000
CN    1738585 A    2/2006
(Continued)

OTHER PUBLICATIONS

International Search Report, PCT/EP2017/073817, dated Jan. 3, 2018.
(Continued)

*Primary Examiner* — Stephone B Allen
*Assistant Examiner* — Rahman Abdur
(74) *Attorney, Agent, or Firm* — Nixon & Vanderhye

(57) ABSTRACT

An optometry device for testing an individual's eye (E) comprises an imaging module (10) adapted to produce a first image at a variable distance for the individual's eye (E), a beam splitter (26) arranged to combine the first image and a second image for the individual's eye (E), and a screen (22) facing the beam splitter (26). A mirror (24) is arranged in combination with the screen (22) to produce the second image to be visible by the individual's eye via the beam splitter (26).

19 Claims, 3 Drawing Sheets

(58) Field of Classification Search
CPC ............... A61B 3/1015; A61B 3/0041; G02B 27/0172; G02B 27/0093; G02B 27/017; G02B 27/10
USPC ........................................................ 351/243
See application file for complete search history.

(56) References Cited

U.S. PATENT DOCUMENTS

| | | | |
|---|---|---|---|
| 4,403,842 | A | 9/1983 | Aulhorn et al. |
| 4,856,884 | A * | 8/1989 | Fender .................. G02B 26/06 359/419 |
| 5,793,469 | A | 8/1998 | Feiertag et al. |
| 6,309,068 | B1 | 10/2001 | Kohayakawa |
| 6,540,356 | B1 | 4/2003 | He |
| 7,438,417 | B2 | 10/2008 | Divo |
| 8,419,184 | B1 * | 4/2013 | Butler .................... A61B 3/103 351/205 |
| 2002/0047997 | A1 | 4/2002 | Hayashi et al. |
| 2006/0103808 | A1 | 5/2006 | Horie |
| 2007/0146630 | A1 | 6/2007 | Divo |
| 2009/0073386 | A1 | 3/2009 | Petito |
| 2009/0153796 | A1 | 6/2009 | Rabner |
| 2011/0075257 | A1 * | 3/2011 | Hua ...................... G02B 26/004 359/464 |
| 2013/0027668 | A1 * | 1/2013 | Pamplona .............. A61B 3/032 351/239 |
| 2016/0331226 | A1 * | 11/2016 | Nauche ................ A61B 3/0285 |

FOREIGN PATENT DOCUMENTS

| | | |
|---|---|---|
| CN | 201058019 Y | 5/2008 |
| CN | 102946790 A | 2/2013 |
| EP | 1 366 706 A1 | 12/2003 |
| EP | 1 686 886 | 8/2006 |
| JP | H06-054805 A | 3/1994 |
| JP | H11-047094 A | 2/1999 |
| JP | 11 244239 | 9/1999 |
| JP | 2002-200041 A | 7/2002 |
| JP | 2003-199712 A | 7/2003 |
| WO | WO 2005/053520 | 6/2005 |
| WO | WO 2015/107303 | 7/2015 |

OTHER PUBLICATIONS

Office Action issued in Chinese Patent Application No. 201780058086.5 dated Feb. 2, 2021.
Office Action issued in Japanese Patent Application No. 2019-515579 dated Jul. 12, 2021.

* cited by examiner

OPTOMETRY DEVICE

TECHNICAL FIELD OF THE INVENTION

The invention relates to the field of optometry. More precisely the invention relates to an optometry device.

BACKGROUND INFORMATION AND PRIOR ART

Optometry devices are used by eye care professionals, in particular optometrists and ophthalmologists, to assist them in assessing characteristics of an individual's vision.

In particular, a refraction apparatus is an optometry device adapted to generate a variable correction and used during a test known as "subjective refraction" in order to determine the necessary correction for compensating an individual's ametropia.

Document U.S. Pat. No. 5,793,469 describes an optometry device for testing an individual's eye comprising an imaging module adapted to produce a first image at a variable distance for the individual's eye, a beam splitter arranged to combine the first image and a second image for the individual's eye and a screen facing the beam splitter.

SUMMARY OF THE INVENTION

In this context, the invention provides an optometry device as just mentioned, characterised by a mirror arranged in combination with the screen to produce the second image to be visible by the individual's eye via the beam splitter.

This makes it possible to project the light beam produced by the screen as a broad virtual image (representing any desired background), upon which the first image is superimposed, thus simulating a realistic situation.

The optometry device may also include one or several of the following optional features (which are to be understood as non limiting):
the mirror is concave;
the imaging module is positioned such that a first light beam corresponding to the first image is transmitted across the beam splitter towards the individual's eye;
the screen and the mirror are positioned such that a second light beam corresponding to the second image is transmitted from the screen to the mirror via the beam splitter, reflects on the mirror towards the beam splitter and reflects on the beam splitter towards the individual's eye;
the screen is a video display;
the optometry device further comprises means for imaging the second image at a second variable distance for the individual's eye;
the optometry device further comprises a variable refraction module interposed between the beam splitter and the individual's eye;
the variable refraction module includes a lens with variable spherical refraction power;
the variable refraction module includes a pair of independently rotatable lenses with cylindrical refraction power;
the optometry device further comprises light sources adapted to illuminate an area situated opposite the individual's eye with respect to the beam splitter;
the optometry device comprises a first housing enclosing the imaging module and a second housing enclosing the beam splitter, the mirror and the screen;

the first image corresponds to an optotype;
the optometry device comprises a casing enclosing the imaging module, the beam splitter, the screen and the mirror;
the optometry device comprises an illuminator adapted to produce a variable ambient light inside the casing.

BRIEF DESCRIPTION OF THE DRAWINGS

The following description will be made in light of the appended figures, where.

DETAILED DESCRIPTION OF EXAMPLE(S)

Figure 1:
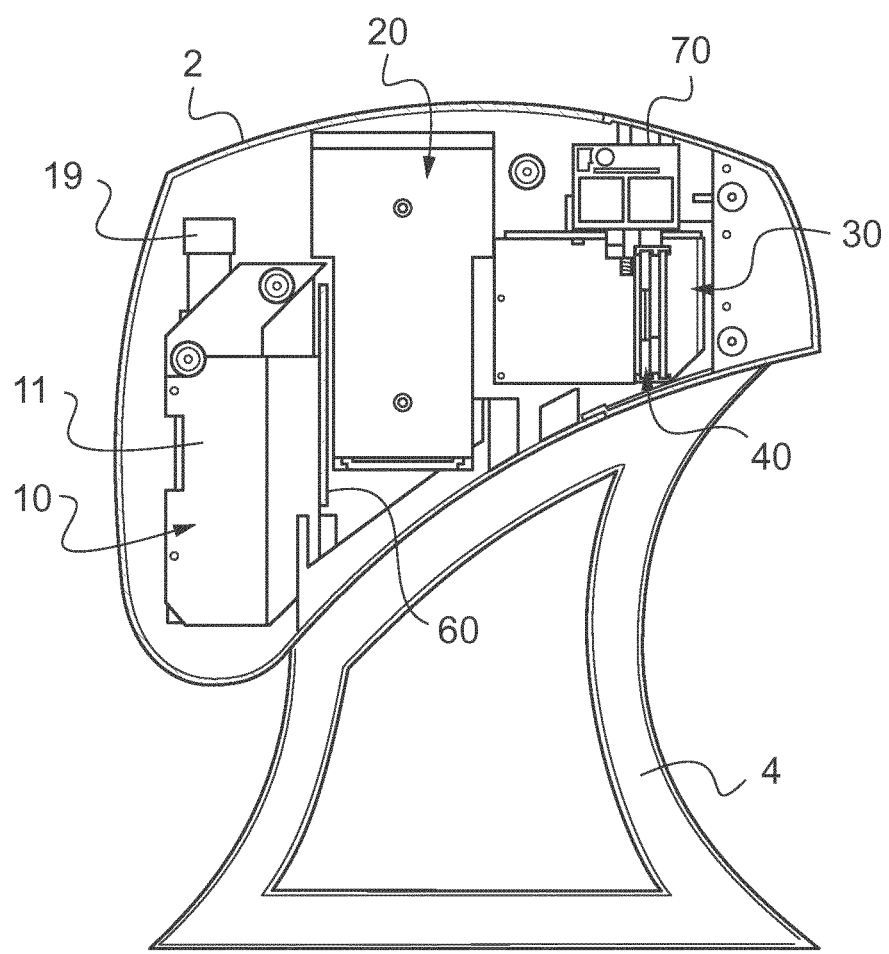
FIG. 1 shows an exemplary optometry device according to the invention.

The optometry device of FIG. 1 includes a casing 2 mounted on a stand 4 so that the optometry device may be placed on a table, for instance.

In the present embodiment, the casing 2 encloses an acuity module 10, a scene module 20, a refraction module 30 and a sensor module 40. The casing 2 also encloses a driving module 70 adapted to move some parts of other modules, in particular some parts of the refraction module 30 (as further explained below) and/or some parts of the sensor module 40.

As visible in FIG. 2, the casing 2 includes a wall 7 situated opposite the acuity module 10 and having a window 8 (possibly closed by a transparent material, such as a transparent plastic) through which an individual can look into the casing 2, as further explained below.

The acuity module 10 includes a screen 12, a pair of mirrors 13, 14, a lens 16 and a further mirror 15.

The screen 12 (for instance an LCD screen) produces a light beam along a screen axis S (this screen axis S being vertical in the present case). As further explained below, this light beam is meant to produce an image of an object, such as an optotype, for an individual using the optometry device.

Mirrors 13, 14 are disposed at a right angle with respect to each other; in addition, mirror 13 is disposed at an angle of 45° with respect to the screen axis S. Thanks to this arrangement, the light beam produced by the screen 12 is successively reflected by mirror 13, then by mirror 14, such that it is directed towards the lens 16 along a lens axis L (the screen axis S and the lens axis L being parallel to each other).

Lens 16 is here an achromatic lens, having a focal length between 200 mm and 300 mm, for instance.

The further mirror 15 is positioned at 45° on the lens axis L, opposite mirror 14 with respect to the lens 16, such that the light beam reflected by mirror 14 along the lens axis L crosses the lens 16 and is then reflected on the further mirror 15 and directed therefrom to the individual's eye E (through window 8) along an optical axis O of the optometry device.

The distance between the lens 16 and the screen 12 (along the optical path just described) is less than the focal length of the lens 16, such that the screen 12 is situated between the object focal plane of the lens 16 and the lens itself.

On the other hand, the casing 2 and the acuity module 10 are designed such that the individual's eye E is situated in the image focal plane of the lens 16 (when the individual positions his head H against a dedicated part of the casing 2).

The acuity module 10 is thus designed to produce an image (representing an object, such as an optotype) for the individual's eye E.

In addition, mirrors 13, 14 are held on a base 18 which is slidably mounted on a support 17 of the acuity module 10 such that mirrors 13, 14 are movable along the (vertical) screen axis S. (The screen 12, the lens 16 and the further mirror 15 are fixedly attached to this support 17.)

Figure 2:
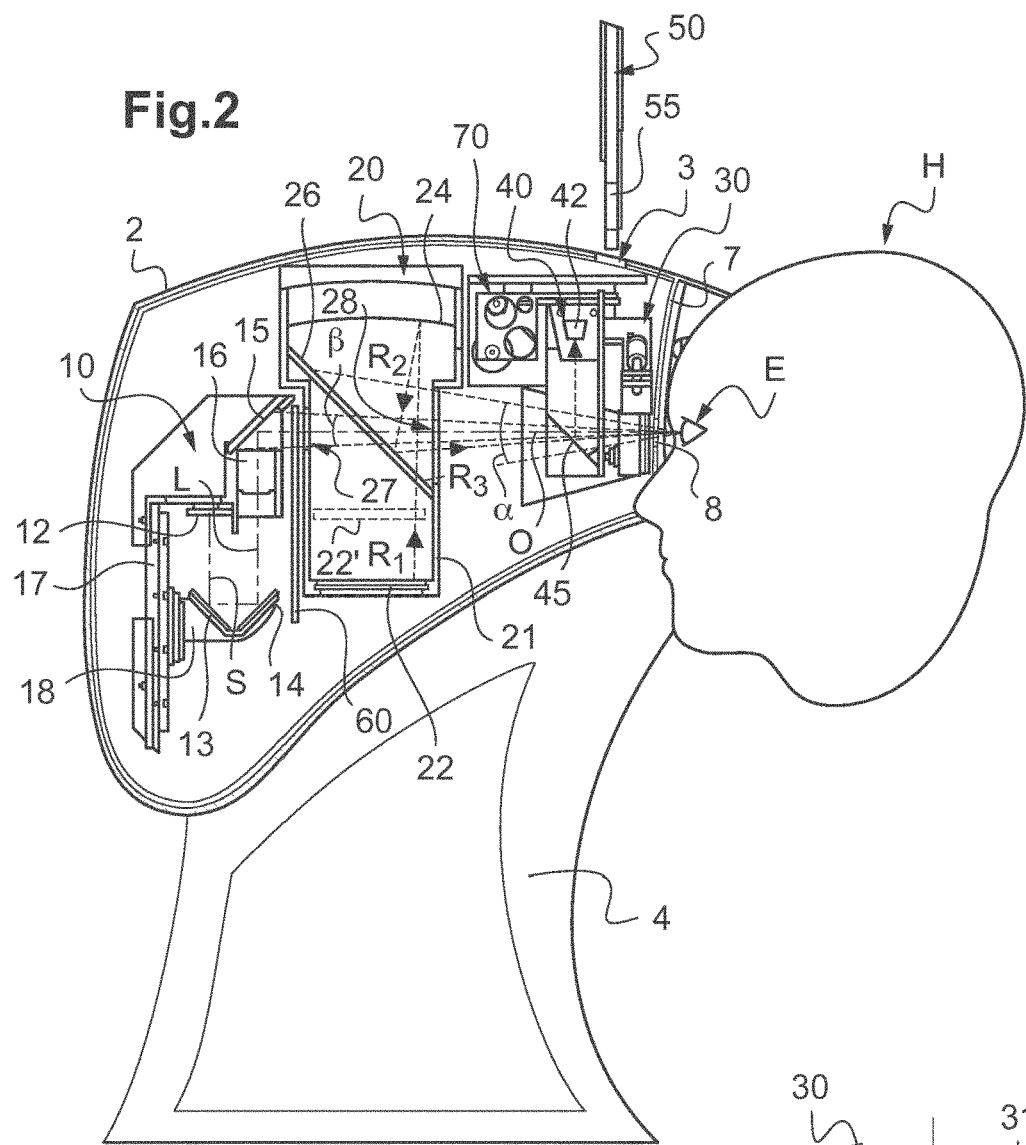
FIG. 2 is a cross section of the optometry device of FIG. 1.

By moving the base 18 carrying mirrors 13, 14 (for instance thanks to an electric motor 19 and associated mechanism, which are not shown in FIG. 2), the length of the optical path between the screen 12 and the lens 16 can be modified.

Thanks to this, the acuity module is adapted to produce the image of the object at a variable distance for the individual's eye E.

The various elements of the acuity module 10 just described are enclosed in a housing 11 shown in FIG. 1 (but not represented in FIG. 2 for the sake of clarity).

The scene module 20 comprises a screen 22, a mirror (here a concave mirror) 24 and a beam splitter 26. The scene module 20 also comprises a housing 21 enclosing the screen 22, the mirror 24 and the beam splitter 26.

The screen 22 may be a video display, for instance an LCD display.

The housing 21 has a first aperture 27 and a second aperture 28, both situated on the optical axis O of the optometry device and meant to allow light directed to the individual's eye E to pass.

The first aperture 27 is made in a wall of the housing 21 facing the acuity module 10, while the second aperture 28 is made in a wall of the housing 21 facing the individual's eye E.

The beam splitter 26 is positioned on the optical axis O. The light beam produced by the acuity module 10 (here, reflected by the further mirror 15 of the acuity module 10) is thus transmitted towards the individual's eye E across the first aperture, the beam splitter and the second aperture.

The screen 22, the beam splitter 26 and the mirror 24 are aligned along a direction (here a vertical direction) perpendicular to the optical axis O. The screen 22 and the mirror 24 are furthermore positioned on either sides of the beam splitter 26, which is itself positioned at 45° with respect to the optical axis.

Thanks to this construction, a light beam produced by the screen 22 is transmitted from the screen 22 to the mirror 24 across the beam splitter 26 (as shown e.g. by ray $R_1$ in FIG. 2), reflects on the mirror 24 towards the beam splitter 26 (ray $R_2$) and reflects on the beam splitter 26 so as to be eventually directed along the optical axis O, towards the individual's eye E (ray $R_3$). This light beam thus also exit the scene module 20 via the second aperture 28.

The (here concave) mirror 24 has a focal length making it possible for the individual using the optometry device to view the image generated by the screen 22 at a distance larger than 5 m (or larger than 6 m).

The beam splitter 26 thus not only makes it possible to transmit the light beam produced by the acuity module 10, but also to add in the same direction (optical axis O) the light beam initially produced by the screen 22 of the scene module 20, i.e. to combine the image produced by the acuity module 10 with another image generated by the screen of the scene module 20.

As visible on FIG. 2, the width of the screen 22 of the scene module 20 (as measured here along the optical axis O) makes it possible to generate a light beam which extends substantially along the whole length of the beam splitter 26 and which is therefore visible from the individual's eye E over a rather wide angle α, generally an angle α of 10° or more, preferably an angle α of 30° or more.

In comparison, the image of the object generated by the acuity module 10 (as visible on the further mirror 15 from the individual's eye E) covers a rather narrow angle β of 5° or less.

In view of this, in the present embodiment, the area of the first aperture 27 is clearly smaller than the area of the second aperture 28.

In the present embodiment, elements of the scene module 20 are positioned such that the (virtual) image produced by the screen 22 of the scene module 20 is in the distance for the individual's eye E (i.e. corresponds to distance vision for the individual).

According to a possible implementation, the screen 22 may be movable (for instance by motorized movement on a linear guide) from the position shown in FIG. 2 to another position (shown in dotted lines under reference 22') in order to image the image produced by the screen 22 at a variable distance for the individual's eye E.

Thanks to the construction of the optometry device presented above, the scene module 20 could be removed (for instance if mounted by detachable means in the casing 2) or not included in some products, without affecting the operation of the acuity module 10 and of other modules 30, 40 described below.

The optometry device may also include an illuminator 60, which is here interposed between the acuity module 10 and the scene module 20. The illuminator 60 may be mounted to the housing 11 of the acuity module, for instance.

The illuminator 60 may comprise at least one light source (for instance a plurality of light sources, such as LEDs) and a plaque of transparent plastic material adapted to scatter and diffuse light. The illuminator 60 is thus adapted to illuminate an area situated opposite the individual's eye E with respect to the beam splitter 26 and therefore to simulate ambient light for the individual. The level of this ambient light (i.e. the simulated luminosity) may be varied by varying the intensity of the light source(s).

The refraction module 30 is mounted in the casing 2 so as to be interposed between the scene module 20 and the individual's eye E (and hence between the acuity module 10 and the individual's eye E).

In the present embodiment, the refraction module 30 is located in the vicinity of the wall 7 of the casing 2 presenting the window 8.

The refraction module 30 is for instance a visual compensation system as described in document WO 2015/107303.

Such a refraction module is adapted to provide a variable optical correction for the individual's eye E looking therethrough.

Figure 3:
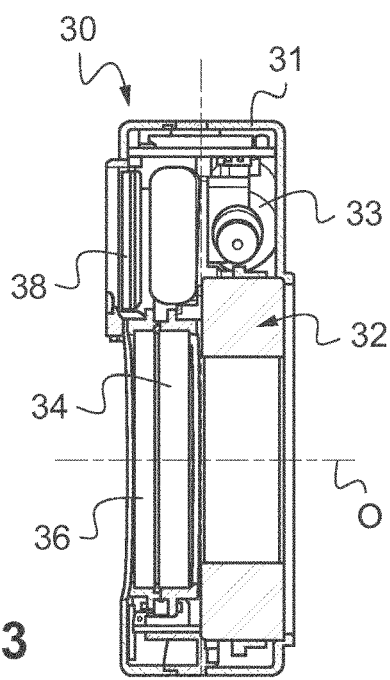
FIG. 3 shows a refraction module possibly included in the optometry device of FIG. 1.

Precisely, as shown in FIG. 3, the refraction module 30 includes a lens 32 having a spherical power along the optical axis O, which spherical power is variable.

Said variable spherical power lens 32 has for instance a deformable surface (such as a deformable membrane). The shape of this surface (in particular the radius of curvature of this surface, and hence the spherical power provided by the lens) can be controlled by moving a mechanical part (such as a ring), which mechanical part may be driven by a first motor 33 of the refraction module 30.

The refraction module also includes a pair of independently rotatable lenses 34, 36 each having a cylindrical power along the optical axis O.

The two rotatable lenses 34, 36 may each be rotated by action of a second motor of the refraction module 30 and of a third motor of the refraction module 30, respectively.

The refraction module 30 includes a control unit 38 which is designed to generate controls for the first motor 33, the second motor and the third motor, respectively, such that the combination of the variable spherical power lens 32 and the two cylindrical power lenses 34, 36 provides a desired spherical correction and a desired cylindrical correction to the individual's eye E, as explained in document WO 2015/107303.

The various elements of the refraction module 30 (such as the variable spherical power lens 32, the cylindrical lenses 34, 36, the first motor 33, the second motor, the third motor and the control unit 38) are enclosed in a housing 31.

In the present embodiment, the optometry device includes two visual compensation systems as mentioned above and shown in FIG. 3, each such system being situated in front of one of the individual's eyes.

The driving module 70 may in this case include means to move each of the visual compensation system in a direction perpendicular to the optical axis O in order to adjust to the pupillary distance (PD) of the individual.

Figure 5:
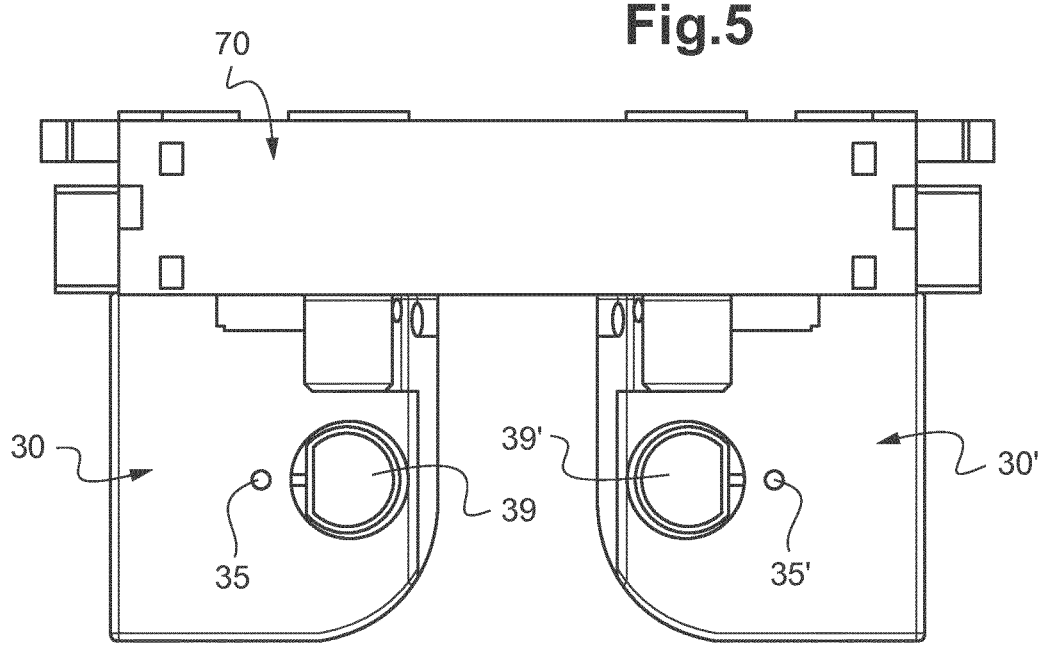
FIG. 5 shows a possible embodiment for refraction modules provided in such an optometry device.

FIG. 5 shows a possible embodiment wherein the optometry device includes two refraction modules 30, 30' and each refraction module 30, 30' is provided with a shutter 39, 39'.

Each shutter 39, 39' is rotatably mounted about an axis 35, 35' (which is substantially parallel to the optical axis O) so as to be movable between a first (closed) position (shown in FIG. 5), where the concerned shutter 39, 39' lies on the optical axis O (i.e. faces window 8) and blocks vision with the concerned eye, and a second (open) position, where the concerned shutter 39, 39' is out of the optical axis O and does not impede vision with the concerned eye.

By controlling the position of the shutters 39, 39' independently and synchronized with the screen 12 of the acuity module 10 and/or the screen 22 of the scene module 20, it is possible to produce an image for the right eye which is distinct from an image produced for the left eye, this being applicable to images produced by the acuity module 10 and to images produced by the scene module.

For instance, for a sequence of images displayed on the screen 12 of the acuity module 10 or on the screen 22 of the scene module 20, odd images can be shown to one eye only (shutter 39 closed, shutter 39' open) while even images are shown to the other eye only (shutter 39 open, shutter 39' closed).

This makes it possible to display stereoscopic images, for instance.

According to a possible embodiment, by displaying images on the screen 12 of the acuity module 10 at moments different than displaying images on the screen 22 of the scene module 20, it also possible to show an image (such as an optotype) produced by the acuity module 10 for a given eye only and to show an image produced by the scene module 20 for both eyes.

The sensor module 40 comprises a beam splitter 45 situated on the optical axis O, tilted at 45° with respect to the optical axis O so as to reflect light emerging from the individual's eye E towards a sensor 42 (situated above the optical axis O in the present case). Sensor 42 is for instance an image sensor, such a video camera, design to capture images of the individual's eye E.

A processing unit, which may be located in the sensor module 40 or elsewhere (e.g. in a distinct electronic apparatus), receives images captured by sensor 42 and analyses these images to deduce therefrom physiological or behavioural parameters relating to the individual, such as the gaze direction of the concerned individual's eye E.

In the present embodiment, the refraction module 30 and the sensor module 40 are positioned in the casing 2 such that a cartridge 50 carrying at least an optical element 55 can be inserted between the refraction module 30 and the sensor module 40.

As shown in FIG. 1, the cartridge 50 is here inserted from above through an opening 3 in the casing 2.

When the cartridge 50 is positioned between the refraction module 30 and the sensor module 40, the optical element 55 is located on the optical axis O such that the individual's eye E observes the beam splitter 26 of the scene module and the further mirror 15 of the acuity module 10 (each producing an image for the individual's eye E) through the optical element 55.

Optical element 55 is for instance a coloured filter, a tinted filter, a polarizing filter or a prismatic lens.

The optometry device described above, although being compact, can simulate real situations thanks to the image generated by the scene module with a broad field of vision.

By simultaneous use of the acuity module 10 and of the scene module 20, a high resolution optotype OPT may be displayed in the centre of an image having a broad field of vision.

When the screen 22 of the scene module 20 is a video display, the test performed using the optometry device can even simulate a moving environment, as in a real situation.

In addition, by enclosing the various elements in the casing 2, as described above, the level of light perceived by the individual's eye E can be adjusted as desired; all kinds of ambient light can thus be simulated (in particular using illuminator 60), from penumbra to dazzling.

A subjective refraction test (possibly using the refraction module 30) can thus be carried out with a light level chosen by the professional, for instance to test photopic vision or mesopic vision.

A test can also be performed for a specific colour (for instance red, green or blue) by displaying images having only the concerned colour on the screen 12 of the acuity module and/or on the screen 22 of the scene module 20.

Optical element 55 may be used for instance to demonstrate interest of using a particular additional filter in a given situation (simulated as described above).

Figure 4:
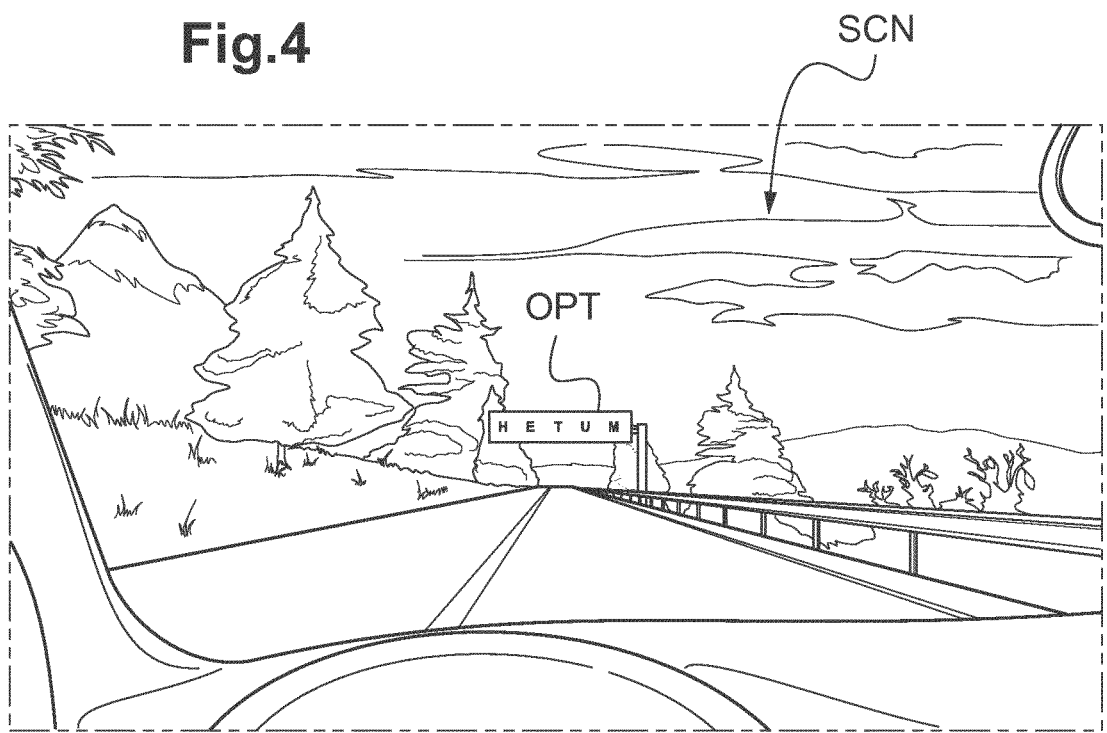
FIG. 4 shows an exemplary view visible by an individual of the optometry device of FIG. 1.

Thanks to the combination of two images (here using the beam splitter 26 of the scene module 20), the object OPT used in the vision test (corresponding to the high resolution image generated by the acuity module 10, e.g. an optotype) is viewed by the individual in the middle of a broader scene SCN (for instance as a distant sign in a landscape), which makes the test more realistic, as in the exemplary view shown in FIG. 4.

For instance, a dedicated subjective refraction test can be performed in a context simulating night driving.

The combination of moving images (produced for instance by the screen 22 of the scene module 20) and the observation of the individual's eye E by the sensor module 40 makes it possible to deduce behavioural features in response to events occurring in the concerned image (here the image produced by the scene module 20). Such a behavioural feature is for instance a response time or a scene exploration strategy. The event may for example be an obstacle moving from a lateral part of the image towards a central part of the image. The behavioural feature measurable by use of the sensor module 40 may in this case be an angle (with respect to the optical axis O) at which the obstacle was detected by the individual (detection being assumed when the gaze direction determined by the sensor module 40 corresponds to the position of the obstacle displayed by the scene module 20).

The invention claimed is:

1. An optometry device for testing an eye of an individual, the optometry device comprising:
    an imaging module configured to produce a first image at a variable distance for the eye of the individual, said imaging module including
        a first screen producing a first light beam, and
        a pair of mirrors successively reflecting the first light beam, disposed at a right angle with respect to each other and held on a base which is slidably mounted on a support of the imaging module;
    a beam splitter configured to combine the first image and a second image for the eye of the individual;
    a second screen facing the beam splitter; and
    an additional mirror disposed in combination with the second screen to produce the second image to be visible by the eye of the individual via the beam splitter, the additional mirror being concave, the second screen and the additional mirror being positioned such that a second light beam corresponding to the second image is transmitted from the second screen to the additional mirror via the beam splitter and reflects on the additional mirror towards the beam splitter.

2. The optometry device according to claim 1, wherein the imaging module is positioned such that the first light beam corresponding to the first image is transmitted across the beam splitter towards the individual's eye of the individual.

3. The optometry device according to claim 2, wherein the second screen and the additional mirror are positioned such that the second light beam corresponding to the second image reflects on the beam splitter towards the eye of the individual.

4. The optometry device according to claim 2, wherein the screen is a video display.

5. The optometry device according to claim 2, further comprising an image device configured to image the second image at a second variable distance for the eye of the individual.

6. The optometry device according to claim 1, wherein the second screen and the additional mirror are positioned such that the second light beam corresponding to the second image reflects on the beam splitter towards the eye of the individual.

7. The optometry device according to claim 6, wherein the screen is a video display.

8. The optometry device according to claim 1, wherein the screen is a video display.

9. The optometry device according to claim 1, further comprising an image device configured to image the second image at a second variable distance for the eye of the individual.

10. The optometry device according to claim 1, further comprising a variable refraction module interposed between the beam splitter and the eye of the individual.

11. The optometry device according to claim 10, wherein the variable refraction module includes a lens with variable spherical refraction power.

12. The optometry device according to claim 10, wherein the variable refraction module includes a pair of independently rotatable lenses with cylindrical refraction power.

13. The optometry device according to claim 1, further comprising light sources configured to illuminate an area situated opposite the eye of the individual with respect to the beam splitter.

14. The optometry device according to claim 1, further comprising:
    a first housing enclosing the imaging module; and
    a second housing enclosing the beam splitter, the additional mirror and the second screen.

15. The optometry device according to claim 1, wherein the first image corresponds to an optotype.

16. The optometry device according to claim 1, further comprising:
    a casing enclosing the imaging module, the beam splitter, the second screen, and the additional mirror; and
    an illuminator configured to produce a variable ambient light inside the casing.

17. The optometry device according to claim 1, wherein the first screen is an LCD screen.

18. An optometry device for testing an eye of an individual, the optometry device comprising:
    an imaging module configured to produce a first image at a variable distance for the eye of the individual;
    a beam splitter configured to combine the first image and a second image for the eye of the individual;
    a screen facing the beam splitter;
    a mirror disposed in combination with the screen to produce the second image to be visible by the eye of the individual via the beam splitter, the mirror being concave, the screen and the mirror being positioned such that a second light beam corresponding to the second image is transmitted from the screen to the mirror via the beam splitter and reflects on the mirror towards the beam splitter.

19. An optometry device according to claim 18, wherein the screen is a video display.

* * * * *